United States Patent [19]

Abram et al.

[11] Patent Number: 4,639,535

[45] Date of Patent: Jan. 27, 1987

[54] TRISUBSTITUTED BENZENE DERIVATIVES AND A METHOD FOR THE PREPARATION THEREOF

[75] Inventors: Trevor S. Abram, Marlow; Peter Norman, Slough; Brian T. Warren, Ickenham, all of England

[73] Assignee: Miles Laboratories, Inc., Elkhart, Ind.

[21] Appl. No.: 792,851

[22] Filed: Oct. 30, 1985

Related U.S. Application Data

[62] Division of Ser. No. 615,042, May 29, 1984, Pat. No. 4,571,405.

[51] Int. Cl.$^4$ .................. C07D 263/04; C07D 309/10
[52] U.S. Cl. ..................................... 549/419; 548/237; 548/238; 548/239
[58] Field of Search .................. 549/419, 23; 548/225, 548/229, 237, 238, 239

[56] References Cited

U.S. PATENT DOCUMENTS 3,933,844  1/1976  Augstein et al. .................. 549/23
3,952,013  4/1976  Hazard et al. .................... 549/23

*Primary Examiner*—Henry R. Jiles
*Assistant Examiner*—J. G. Mullins
*Attorney, Agent, or Firm*—Edward P. Gray

[57] ABSTRACT

Disclosed are trisubstituted benzene derivatives of the formula

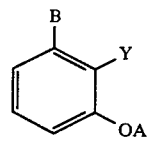

wherein B is selected from the group consisting of —NHCOC(CH$_3$)$_3$, 1,3-oxazolinyl and —CONHR, wherein R is methyl, phenyl, or t-butyl; Y is selected from the group consisting of CO$_2$H, CHO, CO$_2$R' and COR', wherein R' is a lower alkyl having from 1 to 4 carbon atoms; and A is H or tetrahydropyran. Said compounds are valuable intermediates in the preparation of certain anti-allergic chromone or thiochromone-5-oxamic acid derivatives.

4 Claims, No Drawings

TRISUBSTITUTED BENZENE DERIVATIVES AND A METHOD FOR THE PREPARATION THEREOF

This is a division of application Ser. No. 615,042, filed May 29, 1984, now U.S. Pat. No. 4,571,405, issued 2/18/86.

BACKGROUND OF THE INVENTION

I. Field of the Invention

In response to contact with antigens through various allergen mediators, hypersensitive individuals exhibit an altered physiological state resulting in the formation of antigen-specific antibodies. Subsequent contact with one or more of said antigens or a structurally similar substance can evoke, in an allergic individual, various physical responses ranging from minor discomforts such as urticaria and eczema to pathological manifestations such as bronchial asthma.

Allergic responses are involved with the production within an individual of a type of tissue-sensitizing IgE antibody called a reagin. These IgE antibodies have a high affinity for receptors on cells present in various body tissues. The receptors are on mast cells which are found in close association with capillaries in connective tissues throughout the body and on basophilic leukocytes (blood cells). Mast cells and basophils contain a high content of pharmacologically-active mediators or spasmogens, such as histamine, serotonin (5-hydroxytryptamine) and kinins (basic peptides) which are concentrated in cytoplasmic granules. Contact of the IgE antibodies (which are fixed to mast cells and basophils) with antigens can trigger cross-linking of the IgE antibodies. In turn, this cross-linking causes degranulation of mast cells and basophils, which releases the chemical mediators and produces manifestations of the allergic response, e.g., bronchial asthma referred to earlier. In order to reduce the undesirable allergic response, it has been suggested to administer various compounds which have an antiallergic characteristic of interfering with the degranulation of mast cells and basophils.

Antiallergic compounds are often administered parenterally, which involves inconvenience to the patient. There is a need for antiallergic compounds having increased efficacy over known compounds, especially compounds which are orally active.

II. Description of Pertinent Art

U.S. Pat. No. 4,221,800 discloses substituted cycloalkenochromones. Preferred compounds are substituted in the 6 or 7-position. Preferred 6 or 7-substituents are tetrazoyl, methylthio, methylsulfonyl or methylsulfinyl. There is no disclosure of the antiallergenic activity of 5-oxamate-substituted chromones or thiochromones.

U.S. Pat. No. 4,290,954 discloses a large series of cycloalkenochromones; none of the compounds disclosed are 5-oxamates. G.B. Pat. No. 1,561,731 discloses 6 and 7-substituted chromones; 5-oxamate chromones or thiochromones are not described.

SUMMARY OF THE INVENTION

The present invention is directed to certain 5-substituted chromones and thiochromones having antiallergic properties which are represented by the formula:

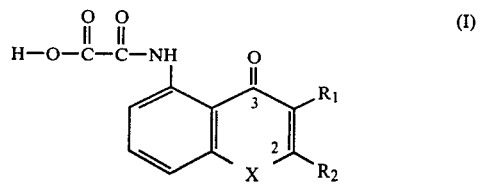

and pharmacologically acceptable nontoxic salts thereof wherein:

X is selected from the group consisting of —O—, —S—, and —$SO_2$—;

$R_1$ and $R_2$ are each independently H or lower alkyl having from 1 to 4 carbon atoms or together with $C_2$ and $C_3$ form a cyclohexane ring having the structure:

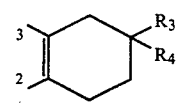

wherein $R_3$ and $R_4$ are each independently H or a lower alkyl having from 1 to 4 carbon atoms.

Also disclosed are valuable intermediates for the preparation of the 5-substituted chromones and thiochromones. Said intermediates are represented by the formula:

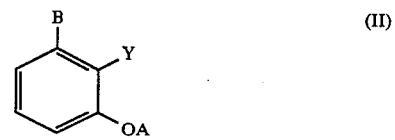

wherein B is selected from the group consisting of —NHCOC($CH_3$)$_3$, 1,3-oxazolinyl and —CONHR, wherein R is methyl, phenyl, or t-butyl; Y is selected from the group consisting of $CO_2H$, CHO, $CO_2R'$ and COR', wherein R' is a lower alkyl having from 1 to 4 carbon atoms; and A is H or tetrahydropyran.

DETAILED DESCRIPTION OF THE INVENTION

The 5-substituted chromones of the present invention are conveniently prepared from a 1,2,3-trisubstituted benzene such as that shown as compound 4 in the illustrative reaction schematic of FIG. 1. The 1,2,3-trisubstituted benzene is prepared by the ortho-lithiation of a 1,3-disubstituted benzene (i.e., compound 3). The 1,2,3-trisubstituted benzene as well as the method of preparation thereof is part of the instant claimed invention.

FIG. 1

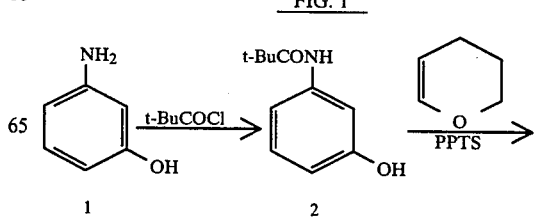

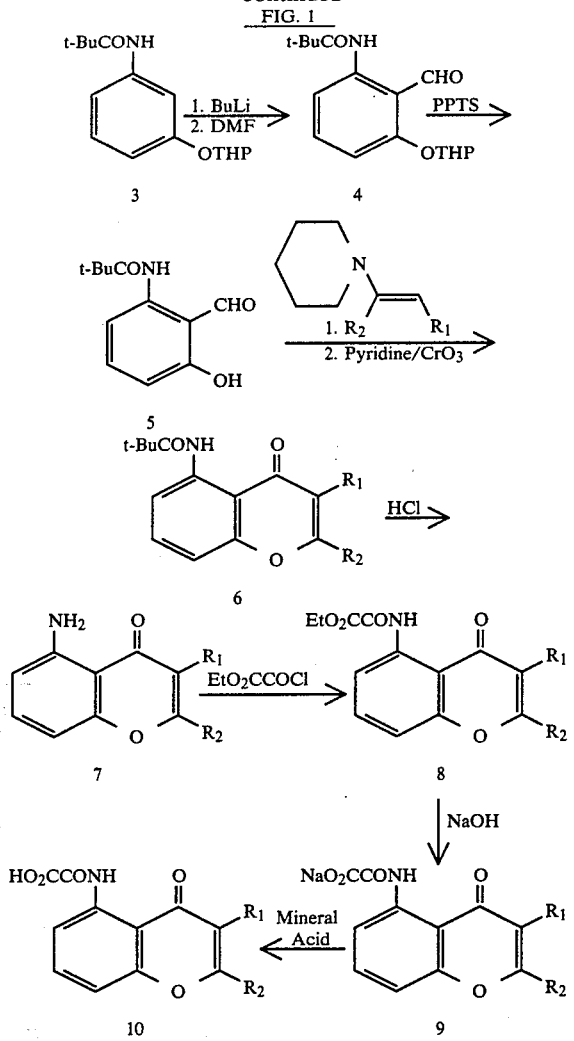

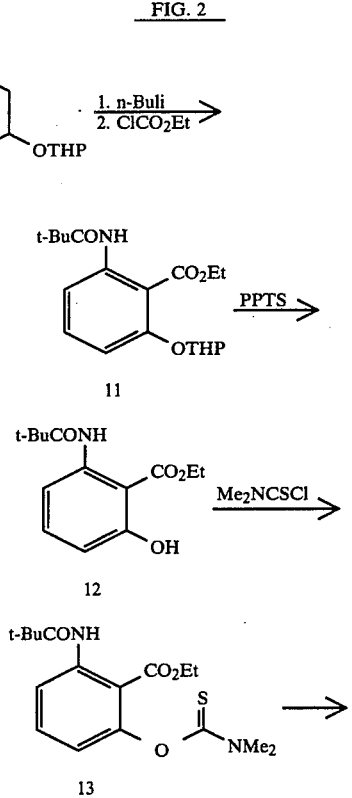

The hydroxyl function of said trisubstituted benzene is then deprotected by refluxing with pyridinium p-toluenesulphonate (PPTS) for a period of time sufficient to render the free salicylaldehyde (5), typically from about 15 to about 60 minutes. Condensation of the free salicylaldehyde with an appropriately $R_1,R_2$-substituted enamine is then accomplished by the method of Paquette and Stucki, *J. Org. Chem.*, 31, 1232 (1966) to render the protected 5-aminochromone (6). The enamine may be, for example, an $R_1,R_2$-substituted piperidine enamine (as shown in FIG. 1), or an $R_1,R_2$-substituted morpholine enamine. The condensation is effected by stirring said enamine with the free salicylaldehyde in an inert organic solvent such as tetrahydrofuran, dimethylformamide or benzene. The crude condensation product may be isolated or alternatively may be directly oxidized with a suitable oxidizing agent, preferably pyridine-chromium trioxide. Subsequent aqueous work-up yields the desired protected 5-aminochromone (6) which is then acid hydrolyzed to give the 5-aminochromone (7). The 5-aminochromone is then treated with a slight molar excess of ethyl oxalyl chloride to form the ethyl oxamate derivative (8). Said ethyl oxamate derivative may then be reacted with sodium hydroxide to form the sodium chromone-5-oxamate (9).

If desired, the sodium chromone-5-oxamate (9) may be readily converted to the corresponding chromone-5-oxamic acid by utilizing readily known techniques such as, for example, by treatment of said chromone-5-oxamate (9) with aqueous mineral acid as described subsequently in Example I.

The 5-substituted thiochromones may be prepared as depicted in the representative reaction schematic of FIG. 2.

As illustrated in FIG. 1, 3-amino phenol (1) is used as a starting material. The use of an amino group instead of, e.g., an acid group, allows easier formation of the oxamate moiety at the 5-position of the chromone or thiochromone. The phenol is reacted with a suitable acylating agent, e.g., trimethylacetyl chloride or t-butylchloroformate, to give the protected amino derivative (2). A preferred protecting group is the pivaloylamino group (t—BuCONH—) which serves to protect the amino moiety as well as "direct" the ortho-substitution at the 3-carbon position of the amino phenol.

The protected amino compound (2) is then reacted with a suitable hydroxy protecting compound such as, for example, acid-catalyzed dihydropyran (dihydropyran and pyridinium p-toluenesulphonate), ethyl vinyl ether, base-catalyzed trialkylsilyl chloride or chloromethyl methyl ether. The dihydropyran is a preferred protecting compound. The resulting disubstituted (diprotected) compound (3) is then lithiated by reaction with an appropriate lithiating agent such as a alkyllithium compound, e.g., n-butyl, sec-butyl or tert-butyl.

The lithiated, diprotected benzene (3) is then treated with an electrophilic reagent to introduce the desired ortho-substituent, e.g., reaction with DMF gives the trisubstituted benzene (4).

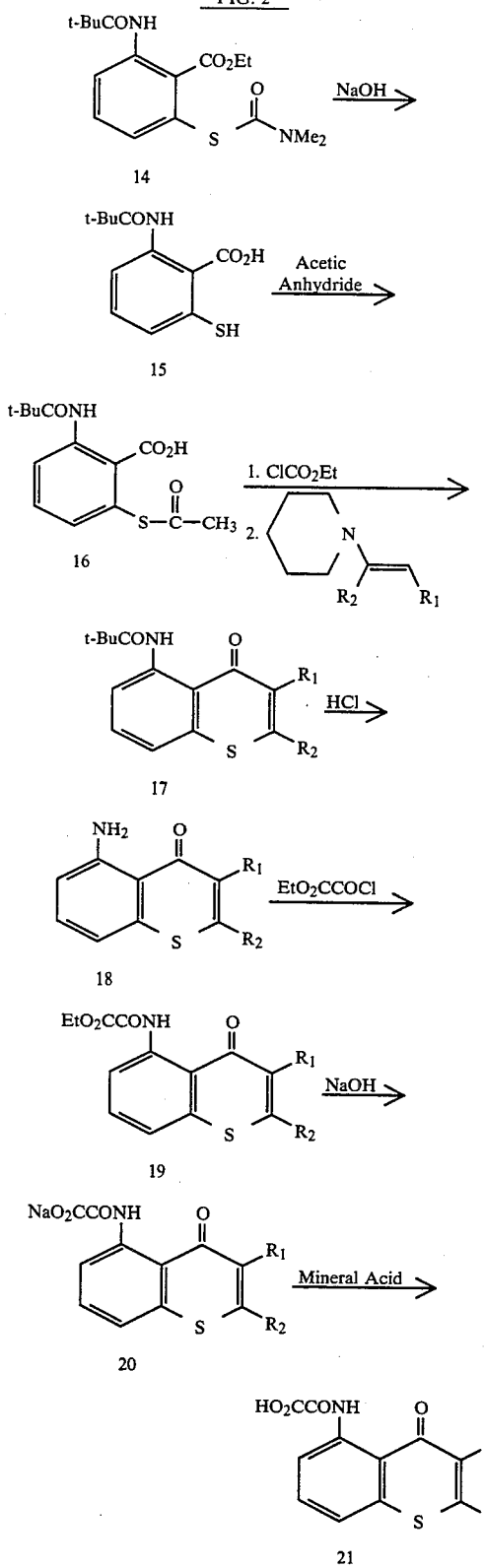

-continued
FIG. 2

The disubstituted benzene (3) is lithiated as described previously for the chromones and reacted with an electrophilic reagent (preferably ethyl chloroformate) to yield the trisubstituted derivative (11). The hydroxyl function is then deprotected by treatment with PPTS to give the phenol (12) which is subsequently converted to the corresponding thiophenol by the method of Newman and Karnes (*J. Org. Chem.*, 31, 3980, 1966). Acylation of the thiophenol (12) with dimethylthiocarbamoyl chloride in an inert solvent in the presence of a hindered base (preferably diazobicyclooctane) gives the carbamate (13). Said carbamate may then be converted into the thiocarbamate (14) by pyrolysis. Hydrolysis of the ester groups with aqueous base gives the thiosalicylic acid (15) which may then be acetylated (preferably with acetic anhydride) to yield the thioacetate (16). This thioacetate (16) may then be reacted with an appropriately $R_1,R_2$-substituted enamine such as an $R_1,R_2$-substituted piperidine enamine, morpholine enamine or pyrrolidine enamine by the method of Boyd, Newson and Hewberry (*J. Chem. Soc.* [C], 935, 1969) to give the protected 5-aminothiochromone (17). Said protected 5-aminothiochromone (17) may then be acid hydrolyzed as described before for the chromone preparation to give the 5-aminothiochromone (18) which is then treated with ethyl oxalyl chloride in a manner similar to that described for the chromone synthesis to yield the ethyl oxamate derivative (19). This ethyl oxamate derivative may then be treated with sodium hydroxide as before to form the sodium thiochromone-5-oxamate (20). If desired, subsequent treatment of this sodium thiochromone-5-oxamate (20) with aqueous mineral acid will form the thiochromone-5-oxamic acid (21).

In addition to the various chromone and thiochromone-5-oxamic acid derivative described herein, certain chromone and thiochromone-5-carboxylic acids and tetrazoles are taught. See examples VII and VIII, below.

The following examples are set forth as a means of illustrating the present invention and are not to be construed as a limitation thereon. All temperatures are reported in degrees centigrade.

EXAMPLE I

Sodium 2,3-cyclohexenochromone-5-oxamate was prepared from 2-N-(2',2'-Dimethylpropanamido)-6-hydroxybenzaldehyde as described below.

(a) A 109.1 g portion (1 mole) of 3-aminophenol was dissolved in dry pyridine (250 ml) and cooled in an ice-bath. Trimethylacetyl chloride (123 ml, 1 mole) was slowly added. After addition was complete, the solution was stirred for 1 hour and then poured into water (750 ml). This was extracted with ether (500 and 2×250 ml), the combined extracts were washed with saturated sodium hydrogen carbonate (250 ml) and brine (2×100 ml), dried over magnesium sulphate and concentrated at reduced pressure to give a sticky fawn solid. Trituration with a mixture of hexane-di-isopropyl ether (300 ml, 1:1) gave an off-white powder. This was collected, washed thoroughly with hexane, then dried in vacuo overnight to give 3-N-(2',2'-Dimethylpropanamido)phenol (155.4 g, 80%), m.p. 135°–138°. An analytical sample was obtained by recrystallization from ethyl acetate-hexane to give white needles, m.p. 142.5°–143°. (Found: C, 68.18; H, 7.64; N, 7.25; Calculated for $C_{11}H_{15}NO_2$: C, 68.37; H, 7.82; N, 7.25).

$\gamma$max (KBr): 3380(NH); 1655, 1535 (CONH) cm$^{-1}$.
$\delta$(CD$_3$)$_2$CO, 90 MHz): 1.27 (s, 9H, (CH$_3$)$_3$C; 3.07 (br, 1H, OH); 6.55 (ddd, 1H, 4-H, $J_{4,5}=7.03$, $J_{4,6}=2.34$, $J_{2,4}=2.05$ Hz); 7.05 (m, 2H, 5-H, 6-H); 7.36 (m, 1H, 2-H); 8.5 (br, 1H, ArNH).

(b) A 96.6 g portion (0.5 mole) of this phenol, dihydropyran (69 ml, 0.75 mole) and pyridinium p-toluenesulphonate (8.3 g, 33 mole) were refluxed in dry dichloromethane (500 ml) for 24 hours. The solution was cooled and washed with dilute sodium hydroxide solution (2×100 ml). The solution was diluted with ether (500 ml) then washed with brine (2×250 ml). The solution was dried with sodium sulphate and concentrated at reduced pressure to give a fawn solid (140 g, quantitative).

This was recrystallized from ethyl acetate-hexane to give tetrahydro-2-[3-[3-(N-2′,2′-dimethylpropanamido)phenoxy]-2H-pyran as white prisms (94.7 g, 68%), m.p. 123°-124°. (Found: C, 69.25; H, 8.22; N, 5.27; Calculated for $C_{16}H_{23}$-$NO_3$: C, 69.30; H, 8.33; N, 5.05).

$\gamma$max (KBr): 3340 (H); 1660s, 1538 (CONH) cm$^{-1}$. $\delta(CD_3)_2CO$, 90 MHz): 1.28 (s, 9H, $(CH_3)_3C$); 1.6–1.95 (m, 6H, 3×$CH_2$); 3.5–4.0 (m, 2H, $CH_2O$); 5.41 (t, 1H, OCHO, J=3 Hz); 6.75 (ddd, 1H, 4-H, $J_{4,5}=7.61$, $J_{2,4}=2.05$, $J_{4,6}=1.85$ Hz); 7.50 (t, 1H, 2-H, J=2.05 Hz); 8.5 (br, 1H, ArNH).

(c) A 22.2 g portion (80 mmole) of the tetrahydropyranyl from above was dissolved in dry tetrahydrofuran (150 ml) and cooled, under argon, in an ice-bath. A solution of n-butyllithium (1.31 M, 128 ml, 0.168 mole) in hexane was slowly added. After addition was complete (2 hours), the yellow solution was stirred a further 2 hours at 0°. Excess dry dimethylformamide (15 ml, 0.194 mole) was then slowly added, dissolved in tetrahydrofuran (40 ml).

The solution was allowed to warm to room temperature, washed with water (2×100 ml) and brine (2×100 ml), dried over magnesium sulphate and concentrated at reduced pressure to give a pale yellow solid (25.5 g, 104%).

This was warmed with hexane (75 ml), cooled and tetrahydro-2-[2-formyl-3-N-(2′,2′-dimethylpropanamido)phenoxy]-2H-pyran collected by filtration as a pale cream powder, m.p. 128.5°-131° (20.7 g). Concentration of the filtrate gave a further quantity of the pyran; the overall yield was 21.6 g, 89% yield.

An analytical sample was recrystallized from ethyl acetate-hexane to give fine white needles, m.p. 134°-134.2° (Found: C, 67.03; H, 7.66; N, 4.64; Calculated for $C_{18}H_{23}NO_4$: C, 66.86; H, 7.60; N, 4.59).

$\gamma$max (KBr): 3240 (NH)- 1685 (CHO); 1640s, 1520 (CONH) cm$^{-1}$. $\delta(CDCl_3$, 90 MHz): 1.35 (2, 9H, $(CH_3)_3C$); 1.7–1.91 (m, 6H, 3×$CH_2$); 3.57–3.75 (m, 2H, $CH_2O$); 5.56 (m, 1H, OCHO); 6.88 (dd, 1H, 4-H, $J_{4,5}=8.57$; $J_{4,cho}=0.7$ Hz): 7.49 (t, 1H, 5-H, J=8.57 Hz); 8.38 (d, 1H, 6-H, $J_{5,6}=8.57$ Hz): 10.60 (d, 1H, ArCHO1, J=0.7 Hz); 11.84 (br, 1H, ArNH).

(d) The pyran compound was converted into the free salicylaldehyde, 2-N-(2′,2′-dimethylpropanamido)-6-hydroxybenzaldehyde as follows.

A 59.6 g portion of the pyran compound (0.195 mole) was dissolved in ethanol (200 ml) and heated to reflux temperature with pyridinium p-toluenesulphonate (5 g) for 40 minutes to give a pale yellow solution.

Excess dilute sodium hydroxide was added to the cooled solution. This was washed with ether (3×150 ml) then acidified with hyrochloric acid and extracted with ether (3×200 ml). The combined extracts were washed with saturated sodium bicarbonate (150 ml), brine (2×250 ml), dried and concentrated at reduced pressure to give the free salicylaldehyde as a pale yellow solid (44.6 g). This was warmed with hexane (100 ml) and cooled, the product was collected by filtration and washed with hexane to give cream needles, m.p. 135°-136° (42.4 g, 98.2%). An analytical sample was recrystallized from toluene-hexane to give cream needles, m.p. 136°-136.5°. (Found: C, 64.49; H, 6.87; N, 6.25; N, 6.25; Calculated for $C_{12}H_{15}NO_3$: C, 65.14; H, 6.83; N, 6.33).

$\gamma$max: 3500–3100 br (OH); 1645 br (CHO-H bonded); 1620s, 1545s (CONH) cm$^{-1}$. $\delta(CDCl_3$, 60 MHz): 1.36 (s, 9H, $(CH_3)_3C$); 6.66 (dd, 1H, 4-H, $J_{4,5}=7.6$, $J_{4,6}$ 1 7.9 Hz); 8.7 (br, 1H, ArOH) 10.40 (s, 1H, ArCHO), 11.28 (s, 1H, ArNH).

(e) A 5.45 g portion (25 mmole) of the salicylaldehyde was dissolved in dry tetrahydrofuran, 1-N-piperidinocyclohexene (6.70 g, 40 mmole) was added and the resultant solution stirred for 30 mins. (The corresponding morpholine enamine, but not the pyrrolidine enamine, may be used.) This was concentrated at reduced pressure to give a yellow glass, then dissolved in dry pyridine (30 ml) and slowly added to a stirred suspension of pyridine-chromium trioxide complex [prepared by careful addition of chromium trioxide (15 g, 0.15 mole) to ice-cooled pyridine (150 ml)]. This was stirred overnight, poured onto ice and extracted with ether (250+2×100 ml), washed with saturated sodium bicarbonate (100 ml) and brine (100 ml), separated and dried with magnesium sulphate and concentrated at reduced pressure to give yellow needles suspended in a brown oil. The crystals were filtered off and washed with ether to give 5-N-(2′,2′-Dimethylpropanamido)-2.3-cyclohexenochromone as white needles, m.p. 216°-217° (2.37 g). The filtrate was concentrated and eluted through alumina (100 ml) with ether-hexane to give a further crop of white needles (0.80 g, overall 42%). These were found to be analytically pure without recrystallization. (Found: C, 71.91; H, 7.44; N, 4.80; Calculated for $C_{18}H_{21}NO_3$: C, 72.21; H, 7.07; N, 4.68).

$\gamma$max (KBr): 1675, 1530s (CONH), 1650s (CO) cm$^{-1}$. $\delta(CDCl_3$, 60 MHz): 1.38 (s, 9H $(CH_3)_3C$); 1.7–1.9 (m, 4H, 2×$CH_2$); 2.4–2.7 (m, 4H, 2×$CH_2$); 6.98 (dd, 1H, 5-H, $J_{5,6}=8$; $J_{5,7}=1.5$ Hz); (5, 1H, 6-H, J=8 Hz); 8.65 (dd, 1H, 7-H; 12.90 (s, 1H, ArNH).

(f) A 4.98 g portion (16.6 mole) of the above amide was refluxed overnight in a mixture of ethanol, water and concentrated hydrochloric acid 2:1:1 (150 ml). On cooling, the solution was neutralized with 5M sodium hydroxide solution and extracted with three portions of ether. The extracts were washed with saturated sodium bicarbonate solution (100 ml) and brine (2×100 ml) dried and concentrated to give the amine, 5-amino-2,3-cyclohexenochromone as an orange solid (3.35 g, 94%). Recrystallization from ethanol gave yellow flakes 2.67 g (76%), m.p. 175°-178°.

(Found: C, 72.14; H, 6.24; N, 6.50; Calculated for $C_{13}H_{13}NO_2$: C, 72.54; H, 6.09; N, 6.51).

$\gamma$max (KBr): 3400, 3300 ($NH_2$); 1643s (CO); 1605 ($NH_2$) cm$^{-1}$. $\delta$($CDCl_3$, 60 MHz): 1.65–1.8 (m, 4H, 2×$CH_2$); 2.4–2.5 (m, 4H, 2×$CH_2$); 6.3–6.6 (br, 2H, $NH_2$); 6.36 (dt, 2H, 5-H, 7-H, J=8, 1.5 Hz); 7.15 (t, 1H, 6-H, J=8 Hz).

(g) A 1.08 g portion (5 mmole) of the above amine was dissolved in dry dimethylformamide (25 ml), triethylamine (0.98 ml, 7 mmole) was added and the solution was cooled in an ice-bath. Freshly distilled ethyl oxalyl chloride (0.78 ml, 7 mmole) was slowly added to give a cream suspension which was stirred for 1 hour. Water (30 ml) was added and the resultant cream solid was collected by filtration and washed with water.

Recrystallization from ethanol gave the ester ethyl 2,3-cyclohexenochromone-5-oxamate as cream flakes, m.p. 172°–173° (1.35 g, 86%). (Found: C, 64.56; H, 5.64; N, 4.48; Calculated for $C_{17}H_{17}NO_5$: C, 64.75; H, 5.43; N, 4.42).

The above ester was hydrolyzed to produce sodium 2,3-cyclohexenochromone-5-oxamate as described below.

(h) A 1.27 g (portion of the above ester (4 mmole) was suspended in ethanol (40 ml) and one equivalent of dilute sodium hydroxide solution was slowly added with vigorous stirring to give a gelatinous mixture. After 2 hours, this was cooled, filtered and washed with ethanol to leave a cream solid. This was recrystallized from aqueous ethanol to give a pale cream powder. Drying in vacuo gave a granular solid identified as the title compound, sodium 2,3-cyclohexenochromone-5-oxamate, m.p. 230° (0.56 g, 45%). (Found: C, 49.51; H, 4.86; N, 3.86; Na, 6.29; Calculated for $C_{15}H_{12}NaNO_5 \cdot 3H_2O$: C, 49.59; H, 4.99; N, 3.86; Na, 6.33).

$\gamma$max (KBr): 3600–3050 ($H_2O$); 1680, 1520s, (CONH); 1645s (CO); 1310s (CO-2) Ccm$^{-1}$. $\delta$(60 mHz, $D_2O$); 1.7 (m, 4H, 2×$CH_2$); 2.1 (m, 2H, 4-$CH_2$); 2.3 (m, 2H, 1-$CH_2$); 6.60 (dd, 1H, 5-H, $J_{5,6}$=8.0, $J_{5,7}$=1.5 Hz); 7.22 (b, 1H, 6-H, J, 8 Hz); 7.91 (dd, 1H, 7-H, $J_{6,7}$=8 Hz).

Acidification of this filtrate with hydrochloric acid gave the free oxamic acid derivative 2,3-cyclohexenochromone-5-oxamic acid as white needles, m.p. 191°–194° (0.36 g, 30%). (Found: C, 61.81; H, 4.76; N, 4.82; Calculated for $C_{15}H_{13}NO_5 \cdot H_2O$: C, 61.74; H, 4.66; N, 4.80).

EXAMPLE II

Sodium 2,3-(4'-ethylcyclohexeno)chromone-5-oxamate was prepared as described below. 2-N-(2',2'-dimethylpropanamido)-6-hydroxybenzaldehyde, the free salicylaldehyde, was prepared as described in Example I, (a)-(d). The salicylaldehyde was converted to 4'-ethyl-5-N-(2',2'-dimethylpropanamido)-2,3-cyclohexenochromone as described in Example I (e), by reaction with 4-ethyl-1-N-piperidinocyclohexene.

This compound was hydrolyzed as described in Example I (f) to give 5-amino-2,3-(4'-ethylcyclohexeno)chromone, m.p. 90°–92°. (Found: C, 73.82; H, 6.97; N, 5.66; Calculated for $C_{17}H_{17}NO_2$: C, 74.05; H, 7.04; N, 5.76).

This amine was reacted with ethyl oxalyl chloride as described in Example I (g), to give the ester ethyl-2,3-(4'-ethylcyclohexeno)chromone-5-oxamate, m.p. 127°–128.5°. (Found: C, 66.3; H, 6.25; N, 3.96; Calculated for $C_{19}H_{21}NO_5$: C, 66.46; H, 6.17; N, 4.08).

Hydrolysis of the ester as described in Example I (h) gave the desired sodium 2,3-(4'-ethylcyclohexeno)chromone-5-oxamate, m.p. 196°. (Found: C, 57.49; H, 5.17; N, 4.01; Calculated for $C_{17}H_{16}NNaO_5$: C, 57.46; H, 5.11; N, 3.94).

EXAMPLE III

Sodium 2,3-(4',4'-dimethylcyclohexeno)chromone-5-oxamate was prepared as described below.

2-N-(2',2'-dimethylpropanamido)-6-hydroxybenzaldehyde was prepared as described in Example I (a)-(d) and converted to 4',4'-dimethyl-5-N-(2',2'-dimethylpropanamido)-2,3-cyclohexenochromone as described in Example I (e) by substituting 4,4-dimethyl-1-N-piperidinocyclohexene for 1-N-piperidinocyclohexene.

This amide was hydrolyzed as described in Example I (f) to give the amine, 5-amino-2,3-(4',4'-dimethylcyclohexeno)chromone.

This amine was reacted with ethyl oxalyl chloride, as described in Example I (g), to give the ester ethyl-2,3-(4',4'-dimethylcyclohexeno)chromone-5-oxamate.

Hydrolysis of the ester as described in Example I (h) gave the desired sodium 2,3-(4',4'-dimethylcyclohexeno)chromone-5-oxamate, m.p. 240°. (Found: C, 57.21; H, 5.13; N, 3.88; Calculated for $C_{17}H_{16}$-$NNaO_5H_2O$: C, 57.46; H, 5.11; N, 3.94).

EXAMPLE IV

Sodium 2,3-dimethylchromone-5-oxamate was prepared as described below.

2-N-(2',2'-dimethylpropanamido)-6-hydroxybenzaldehyde was prepared as described in Example I (a)-(d) and converted to 2,3-dimethyl-5-(2',2'-dimethylpropanamido)chromone as described in Example I (e) by substituting 1-(1-methyl-1-propenyl)-piperidine for 1-N-piperidinocyclohexene.

This compound was hydrolyzed as described in Example I (f) to give the amine, 5-amino-2,3-dimethylchromone, m.p. 149.5°–152°. (Found: C, 69.57; H, 6.05; N, 7.22; Calculated for $C_{11}H_{11}NO_2$: C, 69.82; H, 5.86; N, 7.40).

This amine was reacted with ethyl oxalyl chloride, as described in Example I (g), to give the ester ethyl-2,3-dimethylchromone-5-oxamate, m.p. 171°–173°. (Found: C, 62.03; H, 5.35; N, 4.82; Calculated for $C_{15}H_{15}NO_5$: C, 62.08; H, 5.22; N, 4.84).

Hydrolysis of the ester as described in Example I (h) gave the desired sodium 2,3-dimethylchromone-5-oxamate, m.p. 225°–227°. (Found: C, 51.43; H, 4.26; N, 4.58; Calculated for $C_{13}H_{10}NNaO_5 \cdot 5H_2O$: C, 51.83; H, 4.01; N, 4.65).

EXAMPLE V

Sodium 2,3-(4',4'-dimethylcyclohexeno)thiochromone-5-oxamate was prepared as described below.

(a) Tetrahydro-2-[3-(N-2',2'-dimethylpropanamido)-phenoxy]-2H-pyran was prepared as described in Examples I (a)-(b). This pyran was then converted into ethyl 2-N-(2',2'-dimethylpropanamido)-6-hydroxybenzoate as follows.

(b) A 1.12 g portion of the pyran was lithiated by dissolving said pyran in dry tetrahydrofuran (150 ml) and cooling under argon, in an ice-bath. A solution of n-butyllithium (1.131M, 128 ml, 0.168 mole) in hexane was slowly added with stirring. After addition was complete, approximately 2 hours, the yellow solution obtained was stirred a further 2 hours at 0°.

Freshly distilled ethyl chloroformate was added. Aqueous work-up gave tetrahydro-2-[2-carbethoxy-3-N-(2',2'-dimethylpropanamido)-phenoxy]-2H-pyran as a colorless oil (1.40 g, 100%) which crystallized on prolonged storage at −25°, as white needles, m.p. 62°–63°. (Found: C, 65.14; H, 7.83; N, 4.13; Calculated for $C_{19}H_{27}NO_5$: C, 65.30; H, 7.78; N, 4.00). These crystals slowly reverted to an oil on storage at room temperature.

γmax: 3360 (NH); 1680s ($CO_2Et$ and CONH I); 1530 (CONH II) cm$^{-1}$ (thin film): 1740s ($CO_2Et$), 1680s (CONH I); 1530 (CONH II) cm$^{-1}$. δ(60 MHz): 1.30 (s, 9H, $(CH_3)_3C$); 1.30 (t, 3H, $CH_3CH_2$, J=7 Hz); 1.8–2.0 (m, 6H, 3×$CH_2$); 3.75 (m, 2H, $CH_2O$); 4.30 (q, 2H, $CH_2CH_3$, J=78 Hz); 5.50 (m, 1H, OCHO); 6.95 (dd, 1H, 4-H, $J_{4,5}$=8, $J_{4,6}$=3 Hz); 7.38 (t, 1H, 5-H, J=8 Hz); 8.15 (d, 1H, 6-H), $J_{5,6}$=8 Hz); 9.75 (s, 1H, ArNHCOBu$^t$).

(c) The above tetrahydropyranyl ether (4.1 g) was treated as described in Example I (d) with pyridinium p-toluenesulphonate to produce about 2 g of the free ethyl salicylate as an off-white solid. Recrystallization from diisopropyl ether-hexane gave a cream powder identified as ethyl 2-N-(2',2'-dimethylpropanamido)-6-hydroxybenzoate, m.p. 68°–70°. (Found: C, 65.44; H, 7.30; N, 5.49; Calculated for $C_{14}H_{19}NO_4$: C, 65.35; H, 7.44; N, 5.44).

γmax: 3350 (OH); 1684s ($ArCO_2Et$); 1645s, 1520s (CONH I and II) cm$^{-1}$. d (60 MHz): 1.30 (s, 9H, $(CH_3)_3C$); 1.45 (t, 3H, $CH_3CH_2$, J=7 Hz); 4.55 (q, 2H, $CH_3CH_2O$, J=7); 6.60 (dd, 1H, 4-H, $J_{4,5}$=8, $J_{4,6}$=1.5 Hz); 7.36 (t, 1H, 5-H, J=8 Hz); 8.15 (dd, 1H, 6-H, $J_{5,6}$=8 Hz); 10.3 (br, 1H, ArNH); 10.32 (s, 1H, ArOH, exchanges $D_2O$).

(d) A 12.14 g portion of the above benzoate was dissolved in dry dimethylformamide (100 ml), and diazobicyclooctane (10.28 g) and dimethylthiocarbamoylchloride (8.48 g) were added. The solution was stirred overnight then poured into water (1 liter). Recrystallization from diisopropyl ether gave pale orange prisms (12.37 g, 77%) of ethyl 2-N-(2',2'-dimethylpropanamido)-6-O-(N,N-dimethylthiocarbamoyloxy)-benzoate, m.p. 126°–127°. (Found: C, 58.07; H, 6.84; N, 7.95; S, 9.02; Calculated for $C_{17}H_{24}N_2O_4S$: C, 57.94; H, 6.86; N, 7.95; S, 9.10).

γmax: 1685, 1670s (CO), 1540s (C=S)cm$^{-1}$. δ (60 MHz, acetone): 1.32 (s, 9H, $(CH_3)_3C$); 1.32 (t, 3H, $CH_3CH_2O$, J=7 Hz); 3.28 (s, 3H, $NCH_3$); 3.37 (s, 3H, $\overline{N}CH_3$); 4.28 (q, 2H, $CH_3CH_2O$, J=7 Hz); 6.86 (dd, 1H, 4-$\underline{H}$, $J_{4,6}$=8, $J_{4,5}$=1.5 $\overline{Hz}$); 7.37 (t, 1H, 5$\underline{H}$, J=8 Hz); 8.45 (dd, 1H, 6-H, $J_{5,6}$=8 Hz); 10.7 (br, s, 1H, ArNHCO).

(e) A 16.25 g portion of the above compound was heated, under argon, at 240° for 30 minutes. The dark product that was obtained was triturated with ethanol to give ethyl 2-N-(2',2'-dimethylpropanamido)-6-S-(N,N-dimethylthiocarbamoyloxy)benzoate as a white powder.

Recrystallization from diisopropyl ether-hexane gave white needles, m.p. 101°–103° (11.88 g, 73%). (Found: C, 57.87; H, 6.83; N, 7.95; S, 9.35; Calculated for $C_{17}H_{24}N_2O_4S$: C, 57.94; H, 6.86; N, 7.95; S, 9.19).

γmax: 3360 (NH), 1723s ($CO_2Et$), 1642s ($CONMe_3$) cm$^{-1}$. δ (60 MHz, acetone): 1.28 (s, 9H, $(CH_3)_3C$); 1.33 (t, 3H, $CH_3CH_2O$, J=7 Hz); 2.99 (s, 6H, $(CH_3)_2N$); 4.29 (q, 2H, $CH_3CH_2O$, J=7 Hz); 7.2–7.5 (m, 2H, 4-H, 5-H), 8.35 (dd, 1H, 6-H, $J_{5,6}$=6, $J_{4,6}$=2 Hz); 9.5 (br, 1H, ArNHCO).

(f) A 11.88 g portion of the above benzoate was refluxed for five hours with 5M sodium hydroxide in ethanol (70 ml). The resulting suspension was poured into water, acidified with hydrochloric acid and extracted with ether (3×100 ml).

The combined extracts were washed with brine, dried and concentrated to give 2-N-(2',2'-dimethylpropanamido)-6-mercaptobenzoic acid as a pale yellow syrup (8.55 g, 100%).

γmax: 3490 (NH): 3200–2300 ($CO_2H$); 2580 (SH), 1698 ($CO_2H$) cm$^{-1}$. δ (60 MHz, acetone/DMSO): 1.28 (s, 9H, $(CH_3)_3C$); 6.7–7.1 (br, 2H, $CO_2H$, SH); 7.4 (m, 2H, 4-H, 5-H); 8.3 (m, 1H, 6H); 10.7 (br, 1H, ArNHCO).

(g) A 8.55 g portion of the above mercaptobenzoic acid was dissolved in 50 ml of acetic anhydride and heated at 100° for 4 hours. After cooling, it was poured into water and extracted with ether (3×150 ml). The extracts were washed with brine, dried and concentrated to give an off-white solid which was triturated with diisopropyl ether to give S-Acetyl-2-N-(2',2'-dimethylpropanamido)-6-mercaptobenzoic acid as a white powder, m.p. 80°–81° (5.79 g, 58%). Recrystallization from diisopropyl ether-hexane gave hygroscopic white needles, m.p. 84°–86° (4.81 g, 49%). Because of the hygroscopic nature of the product, elemental analysis was not completely satisfactory. (Found: C, 58.50; H, 5.78; N, 5.10; S, 11.16; Calculated for $C_{14}H_{17}NO_4S$: C, 56.93; H, 5.80; N, 4.74, S, 10.86).

γmax: 3400, 1760, 1690, 1640 cm$^{-1}$. δ (60 MHz, $CDCl_3$): 1.37 (s, 9H, $(CH_3)_3C$); 2.48 (s, 3H, $CH_3CO$); 3.10 (s, 1H, ArNHCO); 6.5 (br, 1H, $CO_2H$); $\overline{7.60}$ (s, 3H, 3×ArH).

(h) A 3.07 g portion of the above mercatobenzoic acid was dissolved in dry chloroform (50 ml) and cooled to 0°. Triethylamine (1.45 ml) was then added and the resulting solution cooled to −5° and ethyl chloroformate (1 ml) was slowly added. After 10 minutes, 4,4-dimethyl-1-N-piperidinocyclohexene (2.01 g) was added and the solution was allowed to warm to room temperature. The solution was refluxed for 48 hours, then the solvent was distilled out and the mixture heated for a further 2 hours. The residue was cooled, slurried in ether, filtered and concentrated to give an orange semi-solid residue (4.65 g). Recrystallization from ethanol gave 4',4'-dimethyl-5-N-(2',2'-dimethylpropanamido)-2,3-cyclohexenothiochromone as fine yellow needles (two crops), m.p. 207°–209° (0.58 g, 16%). (Found: C, 69.68; H, 7.36; N, 4.09; S, 10.00; Calculated for $C_{20}H_{25}NO_2S$: C, 69.89; H, 7.39; N, 4.08; S, 9.33).

γmax: 1672, 1525s (CONH), 1640s (CO) cm$^{-1}$. δ (60 MHz, CDCl$_3$): 1.02 (s, 6H, 2×CH$_3$); 1.36 (s, 9H, (CH$_3$)$_3$C); 1.5-1.7 (m, 2H, 3'-CH$_2$); 2.4 (s, 3H, 5'-CH$_2$); 2.5-2.6 (m, 2H, 2'-CH$_2$); 7.0-7.5 (m, 2H, 7-H, 8-H); 8.75 (d, 1H, 6-H, J$_{6,7}$=8 Hz); 13.5 (br, 1H, ArNHCO).

(j) The above cyclohexenothiochromone was hydrolyzed as described in Example I (f) to give 5-amino-2,3-(4',4'-dimethylcyclohexeno)thiochromone, m.p. 132°-134°. (Found: C, 69.41; H, 6.65; N, 5.35; S, 12.37; Calculated for C$_{15}$H$_{17}$NOS: C, 69.46; H, 6.60; N, 5.40; S, 12.36). The amino chromone compound was reacted with ethyl oxalyl chloride as described in Example I (g) to give as the ester, ethyl 2,3-(4',4'-dimethylcyclohexeno)thiochromone-5-oxamate, m.p. 144°-145°. (Found: C, 63.31; H, 5.90; N, 3.84; S, 9.10; Calculated for C$_{19}$H$_{21}$NO$_4$S: C, 63.49; H, 5.89; N, 3.90; S, 8.92). Hydrolysis of this ester as described in Example I (h) gave sodium 2,3-(4',4'-dimethylcyclohexeno)thiochromone-5-oxamate, m.p. 210°. (Found: c, 53.7; H, 4.4; N, 3.6; S, 9.6; Calculated for: C$_{17}$H$_{16}$NNaO$_4$S.1H$_2$O: C, 53.67; H, 5.00; N, 3.68; S, 8.43).

EXAMPLE VI

Sodium 2,3-(4',4'-dimethylcycloheneno)thiochromone-5-oxamate-1,1-dioxide was prepared as described below.

A 200 g portion of the ester, ethyl-2,3-(4',4'-dimethylcyclohexeno)thiochromone-5-oxamate prepared as described in Example V (i) was dissolved in acetic acid (4 ml) and 30% hydrogen peroxide (0.3 ml) was added to the solution which was refluxed for 30 minutes. The solution was poured into water and extracted with ethyl acetate. The extracts were washed with saturated sodium bicarbonate solution and brine, then dried and concentrated to give ethyl 2,3-(4',4'-dimethylcyclohexeno)thiochromone-5-oxamate-1,1-dioxide as a yellow solid (292 mg, 100%). Recrystallization from isopropanol gave fine yellow needles, m.p. 185°-187° (151 mg, 69%). (Found: C, 58.23; H, 5.46; N, 3.52; S, 8.40; Calculated for C$_{19}$H$_{21}$NO$_6$S: C, 58.30; H, 5.41; N, 3.58; S, 8.19).

Hydrolysis of this ester as described in Example I (h) gave the desired sodium 2,3-(4',4'-dimethylcyclohexeno)thiochromone-5-oxamate-1,1-dioxide, m.p. 250°. (Found: C, 49.7; H, 4.3; S, 8.3; Calculated for: C$_{17}$H$_{16}$NNaO$_6$S.1H$_2$O: C, 49.51; H, 4.64; N, 3.40; S, 7.78).

Other chromones and thiochromones which may be readily prepared by utilizing the techniques disclosed herein include the following compounds.

EXAMPLE VII

Sodium 2,3-cyclohexenochromone-5-carboxylate was prepared as described below.
(a) 2.65 g of the compound prepared in Example I (f) was suspended in dilute hydrochloric acid (30 ml) and a slight excess of sodium nitrite solution was added. The mixture was stirred at 0° for 2 hours to give a clear yellow solution. Anhydrous sodium carbonate was then added to neutralize the solution, which turned maroon.

This maroon solution was added slowly to a cooled aqueous solution of copper (II) cyanide (2.56 g) and sodium cyanide (3.01 g). This was stirred overnight and the precipitated crude nitrile was collected by filtration and washed with water. This was dissolved in boiling chloroform (50 ml) filtered and concentrated at reduced pressure to give 2,3-cyclohexenochromone-5-carbonitrile as a red powder (1.67 g). An analytical sample was recrystallized from ethyl acetate-hexane to give bright orange needles, m.p. 206°-208°. (Found: C, 74.38; H, 5.03; N, 6.24; Calculated for: C$_{14}$H$_{11}$NO$_2$: C, 74.65; H, 4.92; N, 6.22).

γmax (KBr): 2230 (CN)—, 1645s (CO) cm$^{-1}$. δ (60 MHz), CDCl$_3$): 1.6-1.9 (m, 4H, 2×CH$_2$); 2.5-2.8 (m, 4H, 2×CH$_2$); 7.60 (s, 3H, 6-H), 7-H, 8-H).

(b) The above nitrile (0.89 g) was refluxed in acetic acid-sulphuric acid (50 ml) for 3 hours. The solution was cooled and poured into water (50 ml) depositing 2,3-cyclohexenochromone-5-carboxylic acid as pale brown needles, m.p. 218°-222° (δ). An analytical sample was recrystallized from aqueous acetic acid to give yellow flakes, m.p. 219°-221°. (Found: C, 68.40; H, 5.23; Calculated for: C$_{14}$H$_{12}$O$_4$: C, 68.84; H, 4.95).

γmax (KBr): 2300-1750, 1690s (CO$_2$H), 1630s (CO) cm$^{-1}$. δ (60 MHz, (CD$_3$)$_2$SO): 1.8 (m, 4H, 2×CH$_2$); 2.4 (m, 2H, 1-CH$_2$); 2.6 (m, 2H, 4-CH$_2$); 5.5-6.5 (br, 1H, CO$_2$H); 7.30 (dd, 1H, 5-H, J$_{5,6}$=7, J$_{5,7}$=2 Hz); 7.60 (t, 1H, 6-H, J=8 Hz); 7.64 (dd, 1H, 7-H, J$_{6,7}$=9 Hz).

(c) The above carboxylic acid (0.59 g) was warmed with one equivalent of dilute sodium hydrogen carbonate solution. The resultant solution was treated with charcoal, filtered, concentrated at reduced pressure and recrystallized from aqueous ethanol-ether to give fine white needles identified as the title compound sodium 2,3-cyclohexenochromone-5-carboxylate, m.p. 328°-330° (0.42 g, 60%). (Found: C, 57.22; H, 5.29; Na, 8.03; Calculated for: C$_{14}$H$_{11}$NaO$_4$.1.5-H$_2$O: C, 57.33; H, 4.81; Na, 7.83).

γmax (KBr): 3400 (br (H$_2$)), 1640s (CO), 1600 br, 1410s (CO$_2$—) cm$^{-1}$. δ (60 MHz, D$_2$O): 1.7 (m, 4H, 2×CH$_2$); 2.4 (m, 2H, 1-CH$_2$); 2.6 (m, 2H, 4-CH$_2$); 6.95 (dd, 1H, 5-H, J$_{5,6}$=6.7, J$_{5,7}$=1.6 Hz); 7.13 (dd, 1H, 7-H, J$_{6,7}$=9 Hz); 7.62 (dd, 1H, 6-H, J'=6.7, J=1.6 Hz).

EXAMPLE VIII

The sodium salt of 5-(1H-tetrazol-5-yl)-2,3-cyclohexenochromone was prepared as described below.
(a) 0.43 g of the nitrile prepared in Example VII(a), sodium azide (0.52 g) and morpholine hydrochloride (1.00 g) were refluxed for 8 hours in morpholine (50 ml). The cooled solution was poured into water (100 ml) and neutralized with concentrated hydrochloric acid and filtered to give the desired 5-(1H-tetrazol-5-yl)-2,3-cyclohexenochromone as a cream powder, m.p. 227°-229°. Extraction of the filtrate with chloroform gave a further quantity of powder (overall 370 mg). This was recrystallized from acetone to give fine white needles, m.p. 232°-235°. (Found: C, 62.54; H, 4.57; N, 21.08; Calculated for: C$_{14}$H$_{12}$N$_4$O$_2$: C, 62.68; H, 4.51; N, 20.89).

γmax (KBr): 2800-2300 (CHN$_4$), 1639 (CO) cm$^{-1}$. δ (60 MHz), CDCl$_3$): 1.8-2.0 (m, 4H, 2×CH$_2$); 2.5-2.9 (m, 4H, 2×CH$_2$); 7.60 (dd, 1H, 5-H), J$_{5,6}$=7, J$_{5,7}$=2 Hz); 7.79 (t, 1H, 6-H, J=7 Hz); 8.75 (dd, 1H, J$_{6,7}$=7 Hz).

(b) The above tetrazole (0.193 g) was dissolved in one equivalent of dilute sodium hydrogen carbonate solution. The solution was treated with charcoal, filtered and concentrated to dryness to give the title compound 5(1H-tetrazol-5-yl)-2,3-cyclohexenochromone sodium salt as a pale yellow powder, m.p. 283°–285° (d) (0.235 g, 95%). (Found: C, 51.85; H, 4.47; N, 16.84; Na, 6.75; $C_{14}H_{11}NaN_4O_2 2H_2O$ requires C, 51.53; H, 4.63; N, 17.17; Na, 7.04).

$\gamma$max: 3600–3100s br ($H_2O$); 1640s br (CO) $cm^{-1}$. $\delta$ (60 MHz, $D_2O$): 1.6–1.8 (m, 4H, 2×$CH_2$); 2.5 (m 2H, 1-$CH_2$); 2.7 (m, 2H, 4-$CH_2$); 7.12 (dd, 1H, 5-H, $J_{5,6}=7$, $J_{5,7}=2$ Hz); 7.43 (t, 6-H, J=7 Hz); 7.55 (dd, 1H, 7-H, $J_{7,8}=7$ Hz).

The compounds of the present invention are useful in providing relief of allergic conditions, such as asthma in an individual for whom such therapy is indicated. For example, one or more of the compounds can be used prophylactically, to prevent the onset of allergic symptoms. The antiallergic effect is produced by administering to that individual a therapeutically effective antiallergic amount of a compound as presently claimed. The term "individual" as utilized in this specification means a human being or an experimental animal that is a model for a human being. "Therapeutically effective amount" means a dosage or a series of dosages that is effective in producing an inhibition of allergic response in an individual. Medical indications for the use of the antiallergics of the present invention are any conditions in which it is desired to treat allergy or allergic manifestations in an individual. Although the required therapeutic amount will vary from individual to individual and from indication to indication, it is easily determined by one skilled in the art without undue experimentation. Dose forms for the administration of the antiallergic compounds can be prepared by recognized methods in the pharmaceutical sciences and will typically contain from about 0.1 to about 40 percent by weight of one or more of the compounds of formula I. Preferably, the compounds of the present invention may be administered orally, however, other suitable routes of administration such as by inhalation or injection may be utilized.

For oral administration, one or more of the compounds of formula I may be formulated into tablets, hard gelatn or soft elastic capsules, suspensions, emulsions, aqueous and nonaqueous solutions and the like which may be prepared by conventional techniques such as described in *Remington's Pharmaceutical Sciences*, 14th Edition, 1970. For example, tableted dosage forms, in addition to one or more of the compounds of formula I, may also contain various diluents, binders, lubricants, disintegrators or coloring and flavoring agents. Suitable diluents include dicalcium phosphate, calcium sulfate, lactose, kaolin, mannitol, sodium chloride, dry starch and powdered sugar. Examples of binders commonly employed are starch, gelatin, various sugars, methylcellulose, carboxymethylcellulose, polyvinylpyrrolidone and the like. Lubricants such as talc, magnesium stearate, and calcium stearate and disintegrators such as starches, clays, celluloses or gums are also commonly employed.

Further, the pharmaceutical composition may be in a form suitable for administration by inhalation. Such compositions may comprise a suspension or solution of the active ingredient in water or in a suitable alcohol for administration as an aerosol by means of a conventional nebulizer. Alternatively, the compositions may comprise a suspension or solution of the active ingredient in a conventional liquified propellant to be administered as an aerosol from a pressurized container. The compositions may also comprise the solid active ingredient in a solid diluent for administration from a power inhalation device. Other routes of administration, e.g. rectal suppositories, intravenous injection or infusion may also be used.

The pharmaceutical compositions may also contain, in addition to the compound of formula I, other ingredients known to be useful in the prevention or treatment of allergies or allergic manifestations. Such ingredients may include, for example, various antihistamines such as cyproheptadine, pyribenzamine, dexchlorpheniramine maleate, methapyrilene or promethazine; bronchodilators of the $\beta$-adrenergic type such as terbutaline sulfate, metaproperenol, isoetharine mesylate, and isoproterenol as well as other sympathomimetic bronchodilators.

The antiallergic activity of the compounds of the present invention was determined by a passive cutaneous anaphylaxis reaction (PCA reaction) which was conducted as described in *Life Sciences*, 1, p. 465 (1963) and *Immunology*, 12, p. 113 (1967) both of which are incorporated herein by reference. Male Lister-Hooded rats were depilated and injected intradermally with a dilution of rat serum containing IgE antibody against ovalbumin. Twenty-four hours later the rats were challenged with an intravenous injection of the antigen (ovalbumin) and a blue indicator dye. The intensity of the passive cutaneous anaphylactic reaction was determined by observing the size of discrete blue sites (from the indicator) on the backs of the rats. Simultaneous with the challenge, one group of the rats was injected (intravenously) with various concentrations of test compounds (i.e., compounds of formula I), in order to determine the 50 percent inhibitory concentration ($IC_{50}$) for each of said compounds tested. The other group of rats was administered intravenous sodium cromoglycate (SCG), a known antiallergic agent and thus served as a positive control. The results of this test are set forth in Table 1 where the $IC_{50}$ for the test compounds and SCG are expressed in micromoles per kilogram of body weight.

TABLE 1

| INHIBITION OF PCA REACTION ($IC_{50}$ as expressed in micromoles/kilogram) | |
|---|---|
| Compound of Example No. | SCG |
| I[a] | 10.4 | 3.6 |
| II | 15.5 | 2.1 |
| III | 9.6 | 3.6 |
| IV | 5.0 | 1.8 |
| V | 10.0 | 2.1 |
| VI | 16.5 | 2.1 |

[a]The oxamic acid derivative (i.e., 2,3-cyclohexenochromone-5-oxamic acid) with aqueous hydrochloric acid had an $IC_{50}$ of 11.2 micromoles/Kg as compared to 2.4 micromoles/Kg for the SCG control.

Following substantially the same technique as described above, the oral activity of various test compounds (i.e., compounds of formula I) was determined. Thirty minutes prior to the antigen challenge described above, a dose of 30 mg/kg of one of the test compounds was administered intragastrically and the percent inhibition of the percutaneous anaphylactic reaction was determined (as compared to control animals where no test compound was administered). The results of this test are set forth in Table 2 and are expressed as percent inhibition of anaphylaxis relative to control.

TABLE 2

Percent Inhibition of PCA Reaction

| Compound of Example No. | Percent Inhibition |
|---|---|
| I[a] | 27 |
| II | 46 |
| III | 60 |
| IV | 39 |
| V | 14 |
| VI | 27 |

[a]The oxamic acid derivative (i.e., 2,3-cyclohexenochromone-5-oxamic acid) prepared by treatment of the compound of Example I with aqueous hydrochloric acid exhibited a 27 percent inhibition of the PCA reaction.

These data indicate that all compounds tested advantageously exhibited oral antiallergic activity when administered at a concentration of 30 mg/kg. Further, when this same test procedure was repeated using known, orally active antiallergic agents, doxantrazole and proxicromil, less than a ten percent inhibition of the PCA reaction was observed for each compound.

The antiallergic activity of the compounds of the present invention was further demonstrated by measuring the inhibition of allergic release of spasmogen (histamine specifically) from mast cells.

Peritoneal mast cells passively sensitized to antigen (dinitrophenyl-ovalbumin) 24 hours previously were obtained by lavage. Pools of cells were prepared from ten or more rats and aliquots (100 μl) were dispensed into polyethylene tubes. To each tube was added one of the test compounds at a concentration shown in Table 3 together with a constant dose (1 μg) of antigen (dinitrophenyl-bovine serum albumin). Each treatment was repeated in at least three tubes. All of the tubes were incubated at 37° C. for 10 minutes. The mast cells were sedimented by centrifugation and the supernatant fluid removed. The concentration of histamine released as a result of the addition of antigen was determined fluorimetrically and comparisons made with the concentration of histamine released in the absence of drug using the formula:

$$\% \text{ Inhibition of Release} = \frac{d - s}{a - s} \times 100$$

where
d = histamine release in presence of test compound,
a = histamine release in presence of antigen along
and
s = histamine release in presence of saline or drug vehicle (i.e., control).

The results of this test are set forth in Table 3 and are expressed as a percent inhibition of spasmogen release for each concentration (in moles) of the test compound utilized in the above-described procedure.

TABLE 3

Percent Inhibition of Mast Cell Histamine Release

| Compound of Example No. | Concentration (moles) | Percent Inhibitions |
|---|---|---|
| I | $10^{-6}$ | 12.0 |
|  | $10^{-5}$ | 12.6 |
|  | $10^{-4}$ | 10.9 |
|  | $10^{-3}$ | 78.6 |
|  | $10^{-2}$ | 85.7 |
| III | $10^{-6}$ | 8.2 |

TABLE 3-continued

Percent Inhibition of Mast Cell Histamine Release

| Compound of Example No. | Concentration (moles) | Percent Inhibitions |
|---|---|---|
|  | $10^{-5}$ | 10.6 |
|  | $10^{-4}$ | 57.6 |
|  | $10^{-3}$ | 95.1 |
|  | $10^{-2}$ | 92.9 |
| V | $10^{-6}$ | 38.7 |
|  | $10^{-5}$ | 2.7 |
|  | $10^{-4}$ | 40.8 |
|  | $10^{-3}$ | 74.8 |
|  | $10^{-2}$ | 96.7 |
| VI | $10^{-6}$ | 4.4 |
|  | $10^{-5}$ | 3.7 |
|  | $10^{-4}$ | 44.1 |
|  | $10^{-3}$ | 86.9 |
|  | $10^{-2}$ | 95.1 |

These results indicate that all of the compounds tested inhibit mast cell degranulation at a concentration as low as $10^{-6}$ mole. Further, the data suggest that these compounds may be useful in the management of allergic reactions such as bronchial asthma due to inhibition of spasmogen release.

What is claimed is:

1. A compound of the formula:

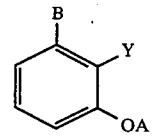

wherein B is selected from the group consisting of —NHCOC(CH$_3$)$_3$, 1,3-oxazolinyl and —CONHR, wherein R is methyl, phenyl, or t-butyl; Y is selected from the group consisting of CO$_2$H, CHO, CO$_2$R' and COR', wherein R' is a lower alkyl having from 1 to 4 carbon atoms; and A is H or tetrahydropyran.

2. The compound of claim 1 which is tetrahydro-2-[2-formyl-3-N-(2',2'-dimethylpropanamido)phenoxy]-2H-pyran.

3. The compound of claim 1 which is Tetrahydro-2-[2-carbethoxy-3-N-(2',2'-dimethylpropanamido)-phenoxy-2H-pyran.

4. A method for preparing the compound of claim 1 comprising the steps of:

(a) reacting 3-aminophenol with an amino-protecting moiety to produce a compound of the formula:

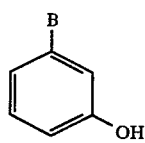

wherein B has the meaning defined above;

(b) reacting the product of (a) with a hydroxy-protecting moiety to produce a compound of the formula:

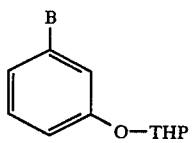

wherein THP refers to tetrahydropyran; and (c) reacting the compound of (b) with a lithiating agent and a compound containing said Y moiety.

* * * * *